United States Patent
Bessalem et al.

(10) Patent No.: US 6,603,036 B2
(45) Date of Patent: Aug. 5, 2003

(54) PROCESS FOR THE MANUFACTURE OF 2-ETHYLHEXYL ACRYLATE

(75) Inventors: Jacqueline Bessalem, Saint-Avold (FR); Michel Fauconet, Valmont (FR); Stephane Lepizzera, Saint-Avold (FR)

(73) Assignee: Atofina, Puteaux (FR)

( * ) Notice: Subject to any disclaimer, the term of this patent is extended or adjusted under 35 U.S.C. 154(b) by 0 days.

(21) Appl. No.: 10/113,924

(22) Filed: Apr. 2, 2002

(65) Prior Publication Data

US 2002/0193623 A1 Dec. 19, 2002

(30) Foreign Application Priority Data

Apr. 2, 2001 (FR) .............................. 01 04442

(51) Int. Cl.⁷ .......................... C07C 69/52; C07C 67/48
(52) U.S. Cl. ...................................... 560/205; 560/218
(58) Field of Search ................... 560/205, 218

(56) References Cited

U.S. PATENT DOCUMENTS

| | | |
|---|---|---|
| 5,510,514 A | 4/1996 | Fauconet et al. |
| 5,659,072 A | 8/1997 | Bessalem et al. |

OTHER PUBLICATIONS

J. Beranek, Refining of acrylic or methacrylic acid esters, Chemical Abstracts, Jun. 25, 1979, vol. 90, No. 26, p. 23.

*Primary Examiner*—Richard L. Raymond
*Assistant Examiner*—Zachary C. Tucker
(74) *Attorney, Agent, or Firm*—Millen, White, Zelano & Branigan, P.C.

(57) ABSTRACT

2-Ethylhexyl acrylate is obtained by esterification of acrylic acid (AA) with 2-ethylhexanol (2-EtHexOH), in the presence of at least one stabilizer for AA, with $H_2SO_4$ as catalyst, the crude reaction mixture (B1) obtained comprising the desired acrylate, 2-EtHexOH, AA, 2-ethylhexyl hydrogensulphate (2-EtHexSO$_4$H), traces of $H_2SO_4$ and impurities. (B1) is washed with water in an extraction column C2 to remove, at the bottom, the aqueous phase (A1), the top organic phase (O2) being sent to a topping column C3 to obtain, at the top, the AA and the 2-EtHexOH, which are recycled to the esterification, the topped desired acrylate being sent to a distillation column C4, from where it exits, purified from the heavy products; a stage of hydrolysis of the 2-EtHexSO$_4$H present in (A1) being carried out to form, in this phase, 2-EtHexOH and $H_2SO_4$, the acidic entities resulting from the hydrolysis being neutralized by introduction of a base into the medium, and the resulting aqueous phase (A3) being sent to the recovery of the 2-EtHexOH in a distillation column C1.

7 Claims, 2 Drawing Sheets

PROCESS FOR THE MANUFACTURE OF 2-ETHYLHEXYL ACRYLATE

The present invention relates to an improved process for the manufacture of 2-ethylhexyl acrylate by a direct esterification of acrylic acid with 2-ethylhexanol, this reaction being catalysed by sulphuric acid.

In this industrial process, to shift the reaction equilibrium, a solvent which azeotropically entrains the water of reaction is not added but this role is provided by an excess of the esterifying alcohol (in this instance, 2-ethylhexanol), which exhibits the distinguishing feature of forming an azeotrope with water.

On conclusion of the reaction stage, which is carried out batchwise, virtually all the sulphuric acid has been converted into 2-ethylhexyl hydrogensulphate (2-EtHexSO$_4$H), according to the following reaction for the esterification of sulphuric acid with 2-ethylhexanol:

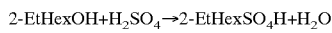

2-EtHexOH+H$_2$SO$_4$→2-EtHexSO$_4$H+H$_2$O

Consequently, the reaction mixture, at the end of the reaction, comprises 2-ethylhexyl acrylate, 2-ethylhexanol, acrylic acid, 2-ethylhexyl hydrogensulphate, traces of sulphuric acid, and the stabilizers conventionally used in the reaction.

In the conventional process, the esterification reaction is followed by purification stages, generally carried out continuously:

- the acidic entities present in the crude reaction mixture are neutralized by addition to the latter of an aqueous solution of a base (sodium hydroxide); during this stage, the acrylic acid is neutralized to sodium acrylate, the 2-ethylhexyl hydrogensulphate to neutral 2-ethylhexyl sulphate 2-EtHexSO$_4$Na, and the traces of sulphuric acid to sodium sulphate Na$_2$SO$_4$, all these salts passing into the aqueous phase;
- the separated organic phase resulting from the neutralization is washed with water in an extraction column, in order to remove the traces of impurities, of sodium hydroxide and of salts, and then the washed 2-ethylhexyl acrylate is conveyed to a first distillation column which makes it possible to remove, at the top, the light products, which light products are recycled to the esterification reaction; the topped ester is subsequently conveyed to a second column, from where it emerges at the top, purified from the heavy products;
- the 2-ethylhexanol, present:
  - in the separated aqueous phase resulting from the neutralization, which essentially comprises neutral 2-ethylhexyl sulphate, 2-ethylhexanol, sodium acrylate and traces of sodium sulphate,
  - in the aqueous phase resulting from the esterification reaction proper, and
  - in the aqueous phase resulting from the washing of the organic phase in the extraction column, is recovered, this recovery of the 2-ethylhexanol being carried out in a distillation column fed at the top with the aqueous liquors to be treated, in which column the 2-ethylhexanol is entrained at the top and can be recycled to the esterification reaction, whereas the column bottom product constitutes the waste aqueous liquors, freed from the 2-ethylhexanol, which will be discharged to the biological treatment plant.

As the aqueous liquors thus discharged are highly polluted with organic matter (measured by the chemical oxygen demand (COD)) because of the presence of neutral 2-ethylhexyl sulphate and sodium acrylate, an improved process for the manufacture of 2-ethylhexyl acrylate has been developed, which process forms the subject-matter of European Patent Application EP-A-609 127.

As may be described with reference to FIG. 1 in the appended drawing, in accordance with this known process, the reaction mixture (b1) is, as in the conventional process, neutralized with a sodium hydroxide solution and, on conclusion of this neutralization, the mixture separates on settling into two phases: an aqueous phase (a1) and an organic phase (o1).

After addition of sulphuric acid to (a1), in order to obtain a molar ratio of the number of H$^+$ equivalents in excess to the number of moles of 2-ethylhexyl hydrogensulphate at least equal to 1.5, the new mixture (a2) is introduced into a hydrolysis reactor R$_{HYD}$ and brought to a temperature of the order of 70–200° C. for a time of the order of 1–5 hours. The mixture, after reaction, is neutralized to pH 8 with 8% NaOH. The resulting phase (a3) is sent continuously to a distillation column C1 for recovery of the 2-ethylhexanol at the top and concentration at the bottom of the exhausted aqueous liquors intended for the biological treatment.

After a further neutralization with NaOH, the separated organic phase (o1) is washed with water in an extraction column C2 in order to remove the traces of impurities, of sodium hydroxide and of salts. The aqueous phase (a4) resulting from the bottom of the extraction column C2 is sent to a distillation column C1.

The washed 2-ethylhexyl acrylate obtained at the top of the column C2 is sent to a first distillation column C3 which makes it possible to remove, at the top, the light products composed essentially of 2-ethylhexanol, which products are recycled to the esterification reaction. The topped 2-ethylhexyl acrylate, obtained at the bottom, is sent to the second distillation column C4, from where it exits at the top, purified from the heavy products.

During the implementation of this process for the manufacture of 2-ethylhexyl acrylate, it appears that a dense emulsion is formed at the interphase during the separation by settling which takes place subsequent to the abovementioned neutralization stage. This emulsion, which might be due to 2-ethylhexyl acrylate polymers growing at the interphase, disrupts the downstream distillation line and lowers the environmental performance of the manufacturing plant.

The stage of neutralization of the crude reaction mixture generates most of the COD of the plant due to the sodium acrylate, which originates, on the one hand, from the neutralization of the unconverted acrylic acid and, on the other hand, from the saponification of the 2-ethylhexyl acrylate.

The inventors have discovered that these problems can be solved without chemical treatment by the suppression of the neutralization with NaOH of the phases (b1) and (o1), the 2-ethylhexyl hydrogensulphate being removed by washing with water and separating by settling in the column C2, the residual acrylic acid not extracted into the aqueous phase as was the case in the known process according to EP-A-609 127, being removed at the top of the topping column C3.

A subject-matter of the present invention is therefore a process for the manufacture of 2-ethylhexyl acrylate by direct esterification of acrylic acid with 2-ethylhexanol in the presence of at least one stabilizer for acrylic acid, the said esterification being catalysed by sulphuric acid, the crude reaction mixture (B1) obtained comprising 2-ethylhexyl acrylate, 2-ethylhexanol, acrylic acid, 2-ethylhexyl hydrogensulphate, traces of sulphuric acid and the usual impurities, characterized in that the crude reaction mixture (B1) is washed with water in an extraction column C2 which makes it possible to obtain, at the top, an organic phase (O2) and to remove, at the bottom, an aqueous phase (A1), the organic phase (O2) being sent to a topping column C3 which makes it possible to obtain, at the top, the acrylic acid and the 2-ethylhexanol present in the phase (O2), which products are recycled to the esterification reaction, the topped 2-ethylhexyl acrylate being sent to a second distillation column C4, from where it emerges at the top, purified from the heavy products; and the aqueous phase (A1) being sent to a stage of hydrolysis of the 2-ethylhexyl hydrogensulphate present in the said aqueous phase (A1), the hydrolysis being carried out so as to form, in the said phase, 2-ethylhexanol and sulphuric acid, the acidic entities resulting from the said hydrolysis being neutralized by introduction of a base into the medium, and the resulting aqueous phase (A3) being sent to a stage of recovery of the 2-ethylhexanol in a distillation column C1, the said alcohol being entrained into the top of the said column C1.

In accordance with specific embodiments of the process according to the invention:

the washing of the crude reaction mixture (B1) with water is carried out with the use of 5 to 50% by weight of water with respect to the charge of crude reaction mixture (B1); furthermore, this stage of washing the crude reaction mixture (B1) with water is generally carried out at a temperature of 20–50° C.; and the hydrolysis is carried out at a temperature of between 70 and 200° C.

To give a better illustration of the subject-matter of the present invention, an implementational example (Example 1) thereof will be described below with reference to FIG. 2 of the appended drawing, which represents the diagram of the process according to the invention. Comparative Example 2 is presented with reference to the abovementioned FIG. 1, which figure illustrates the known process. In the examples, the parts and percentages are by weight.

The progression of the various streams illustrated in FIGS. 1 and 2 has been described above.

The entire disclosure[s] of all applications, patents and publications, cited above or below, and of corresponding French Application No. 01.04442, filed Apr. 2, 2001 are hereby incorporated by reference.

EXAMPLES

Figure 1:
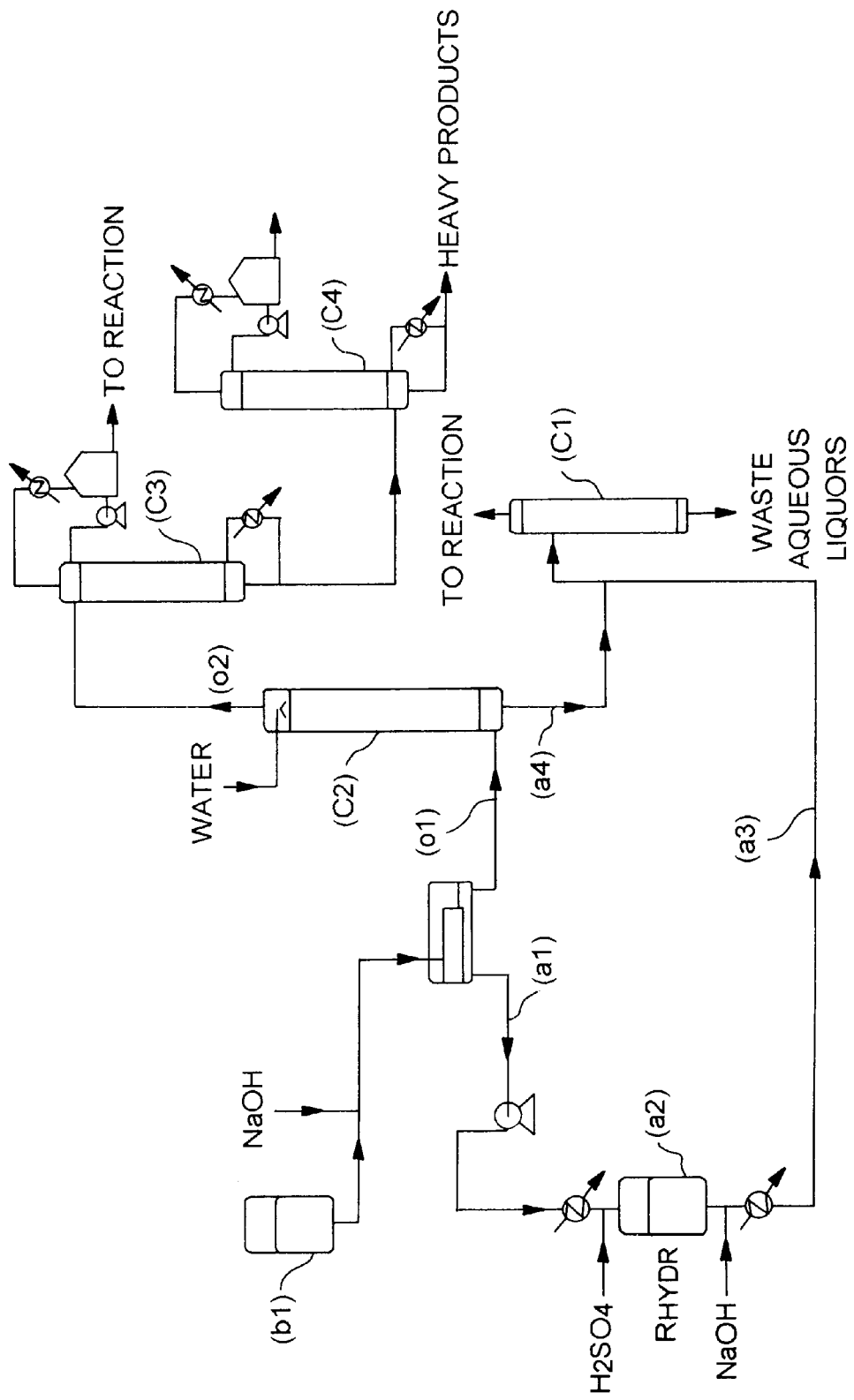
FIG. 1 depicts a known process.
Figure 2:
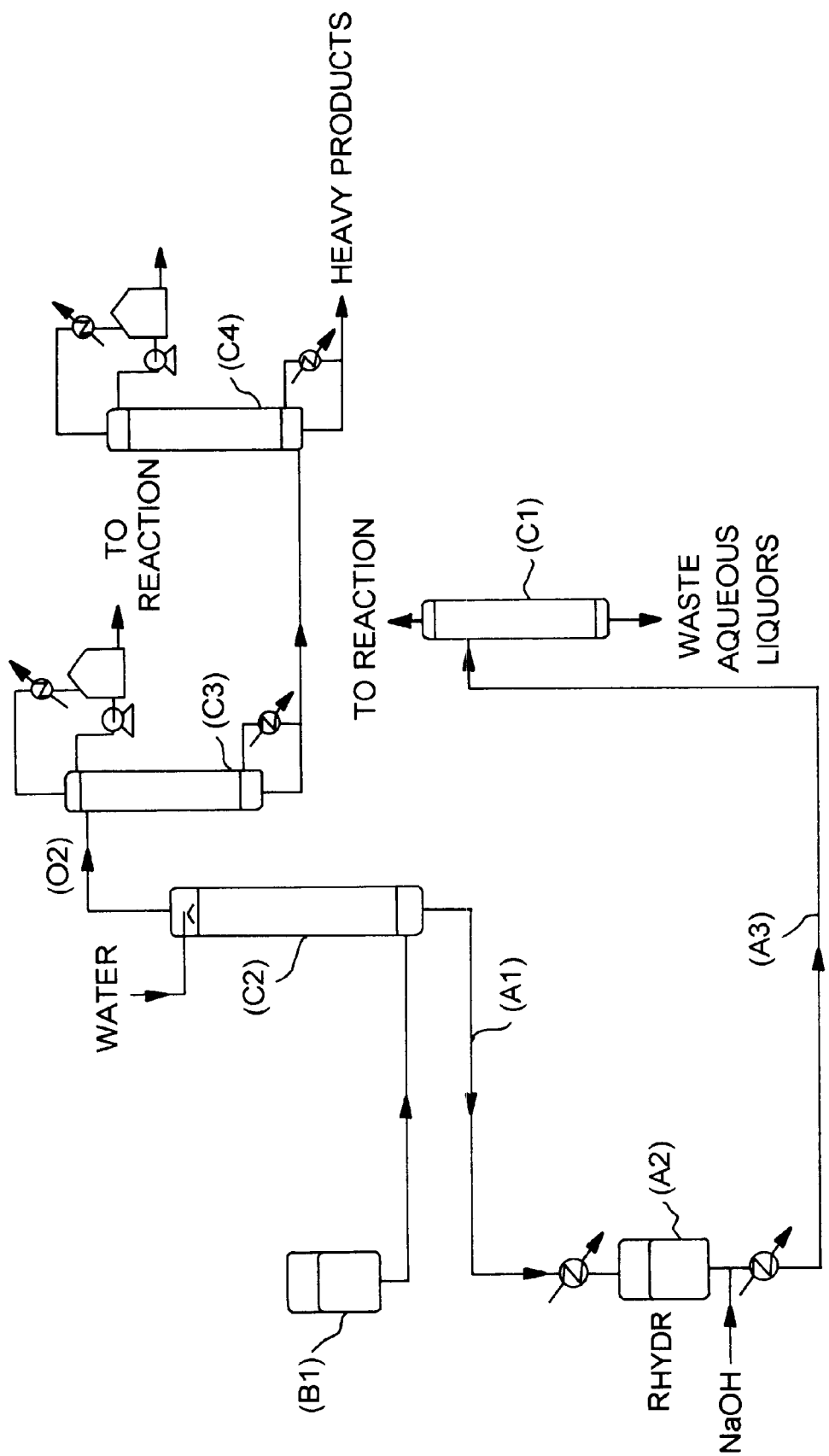
FIG. 2 depicts an embodiment of the process of the invention.

In the foregoing and in the following examples, all temperatures are set forth uncorrected in degrees Celsius; and, unless otherwise indicated, all parts and percentages are by weight.

Example 1 of the Invention

A—Synthesis of the Crude Reaction Mixture

Acrylic acid (466.3 parts) is esterified, batchwise, with 2-ethylhexanol (520 parts), in the presence of 94% sulphuric acid (9.76 parts) as catalyst and in the presence of phenothiazine as polymerization inhibitor (0.7 part), in a stirred reactor at a temperature of 90° C. under reduced pressure. The equilibrium of the esterification reaction is shifted towards the formation of the expected 2-ethylhexyl acrylate ester by distillation of the water generated, in the form of an azeotropic mixture with the 2-ethylhexanol.

The composition of the crude reaction mixture (B1) is as follows:

| | |
|---|---|
| 2-Ethylhexyl acrylate | 91% |
| 2-Ethylhexanol | 4.4% |
| Acrylic acid | 0.5% |
| 2-Ethylhexyl hydrogensulphate | 2.5% |
| Water | 0.5% |
| Other impurities | 1.1% |

B—Extraction of the Catalyst by Washing Three Times with Water Simulation of the Column C2

46 g of water are added to 460 g of crude reaction mixture (B1) comprising the catalyst (0.12 eq. $H^+$/kg of high acidity—2-ethylhexyl hydrogensulphate) and stirring is carried out at ambient temperature for 10 minutes. After separating by settling, 452 g of organic phase (O1) comprising 0.011 eq. $H^+$/kg of high acidity are recovered.

The efficiency of extraction of the catalyst is 91%.

This operation is repeated twice (treatment of the organic phase (O1) with 10% of water by weight), so as to simulate the operation of the column C2.

At the outlet of column C2, the washed crude reaction mixture (O2) comprises $6'10^{-5}$ $H^+$/kg.

The overall efficiency of extraction of the catalyst is 99.5%.

C—Purification of the Crude Mixture (O2)

(O2) is conveyed to the column C3, to exit, at the top:

the acrylic acid and the 2-ethylhexanol essentially; and, at the bottom:

the 2-ethylhexyl acrylate comprising the stabilizer and the heavy products (essentially ester of the dimer of acrylic acid and octyl octoxypropionate).

The bottom product from this column C3 is conveyed to the column C4, to exit, at the top of C4, the pure 2-ethylhexyl acrylate (purity 99.7%).

H—Hydrolysis of the Aqueous Phases (A1) and (A5)

The aqueous phase (A1) resulting from the column C2 is conveyed to the hydrolyser $R_{HYD}$ to decompose the 2-ethylhexyl hydrogensulphate to $H_2SO_4$ and 2-ethylhexanol (T=130° C.; time=2 hours; pressure: 2–3 bar).

The stream exiting from the hydrolyser $R_{HYD}$ is neutralized with NaOH and conveyed to the column C1 to recover, at the column top, the 2-ethylhexanol.

Example 2

Comparative

The process was carried out as described with reference to FIG. 1, this process employing the neutralization of the crude reaction mixture (b1) having the same composition as (B1). This process resulted in a dense emulsion during the neutralization stage and in the loss of the acrylic acid.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. Process for the manufacture of 2-ethylhexyl acrylate by direct esterification of acrylic acid with 2-ethylhexanol in the presence of at least one stabilizer for acrylic acid, the said esterification being catalysed by sulphuric acid, the crude reaction mixture (B1) obtained comprising 2-ethylhexyl acrylate, 2-ethylhexanol, acrylic acid, 2-ethylhexyl hydrogensulphate, traces of sulphuric acid and the usual impurities, characterized in that the crude reaction mixture (B1) is washed with water in an extraction column C2 which makes it possible to obtain, at the top, an organic phase (O2) and to remove, at the bottom, an aqueous phase (A1), the organic phase (O2) being sent to a topping column C3 which makes it possible to obtain, at the top, the acrylic acid and the 2-ethylhexanol present in the phase (O2), which products are recycled to the esterification reaction, the topped 2-ethylhexyl acrylate being sent to a second distillation column C4, from where it emerges at the top, purified from the heavy products; and the aqueous phase (A1) being sent to a stage of hydrolysis of the 2-ethylhexyl hydrogensulphate present in the said aqueous phase (A1), the hydrolysis being carried out so as to form, in the said phase, 2-ethylhexanol and sulphuric acid, the acidic entities resulting from the said hydrolysis being neutralized by introduction of a base into the medium, and the resulting aqueous phase (A3) being sent to a stage of recovery of the 2-ethylhexanol in a distillation column C1, the said alcohol being entrained into the top of the said column C1.

2. Process according to claim 1, characterized in that the washing of the crude reaction mixture (B1) with water is carried out with the use of 5 to 50% by weight of water with respect to the charge of crude reaction mixture (B1).

3. Process according to claim 1 characterized in that the washing of the crude reaction mixture (B1) with water is carried out at a temperature of 20–50° C.

4. Process according to claim 1 characterized in that the hydrolysis is carried out at a temperature of between 70 and 200° C.

5. Process according to claim 2, characterized in that the washing of the crude reaction mixture (B1) with water is carried out at a temperature of 20–50° C.

6. Process according to claim 2, characterized in that the hydrolysis is carried out at a temperature of between 70 and 200° C.

7. Process according to claim 3, characterized in that the hydrolysis is carried out at a temperature of between 70 and 200° C.

* * * * *